US012610899B2

(12) United States Patent
Eskola et al.

(10) Patent No.: US 12,610,899 B2
(45) Date of Patent: Apr. 28, 2026

(54) SPREADING DEVICE, METHOD AND POWDER-LIKE MIXTURE COMPOSITION FOR CONTROLLING OR PREVENTING FOREST PATHOGENS ON TREE STUMPS

(71) Applicant: Danstar Ferment AG, Zug (CH)

(72) Inventors: Lauri Eskola, Koria (FI); Pekka Seiskari, Luoma (FI)

(73) Assignee: Danstar Ferment AG, Zug (CH)

( * ) Notice: Subject to any disclaimer, the term of this patent is extended or adjusted under 35 U.S.C. 154(b) by 676 days.

(21) Appl. No.: 17/874,034

(22) Filed: Jul. 26, 2022

(65) Prior Publication Data

US 2022/0354071 A1 Nov. 10, 2022

Related U.S. Application Data

(62) Division of application No. 16/276,827, filed on Feb. 15, 2019, now Pat. No. 11,432,480.

(30) Foreign Application Priority Data

Feb. 15, 2018 (FI) ...................................... 20185135

(51) Int. Cl.
| | |
|---|---|
| *A01G 23/099* | (2006.01) |
| *A01G 7/06* | (2006.01) |
| *A01M 9/00* | (2006.01) |
| *A01N 25/08* | (2006.01) |
| *A01N 25/12* | (2006.01) |
| *A01N 63/30* | (2020.01) |
| *C12N 1/145* | (2026.01) |

(52) U.S. Cl.
CPC ............. *A01G 23/099* (2013.01); *A01G 7/06* (2013.01); *A01M 9/0007* (2013.01); *A01M 9/0053* (2013.01); *A01N 25/08* (2013.01); *A01N 25/12* (2013.01); *A01N 63/30* (2020.01); *C12N 1/145* (2021.05)

(58) Field of Classification Search
None
See application file for complete search history.

(56) References Cited

U.S. PATENT DOCUMENTS

| | | | |
|---|---|---|---|
| 3,070,263 A | 12/1962 | Mcmullen | |
| 3,832,803 A | 9/1974 | Blake et al. | |
| 4,071,170 A | 1/1978 | Gunzel, Jr. et al. | |
| 4,089,441 A | 5/1978 | Cole et al. | |
| 7,754,653 B2 * | 7/2010 | Hintz .................... | D21C 5/005 |
| | | | 504/117 |
| 8,726,567 B1 | 5/2014 | Pishdadian et al. | |
| 10,681,874 B1 | 6/2020 | Scarlata | |
| 2008/0107689 A1 * | 5/2008 | Seiskari .................. | C12N 1/04 |
| | | | 424/274.1 |
| 2012/0261032 A1 | 10/2012 | Raszga et al. | |

| | | | |
|---|---|---|---|
| 2015/0083755 A1 | 3/2015 | Mecker et al. | |
| 2016/0165889 A1 | 6/2016 | Goertz et al. | |
| 2016/0278384 A1 * | 9/2016 | Jabs ...................... | A01N 63/30 |
| 2018/0317474 A1 | 11/2018 | Hikosaka et al. | |
| 2019/0008158 A1 | 1/2019 | Von Maltzahn | |
| 2019/0124865 A1 | 5/2019 | Sunnen | |
| 2019/0191631 A1 | 6/2019 | Regan et al. | |
| 2020/0120886 A1 | 4/2020 | Geltner | |
| 2020/0141079 A1 | 5/2020 | Kijlstra et al. | |

FOREIGN PATENT DOCUMENTS

| | | |
|---|---|---|
| CA | 875912 A | 7/1971 |
| CN | 202722340 U | 2/2013 |
| CN | 203058162 U | 7/2013 |
| CN | 104877937 A | 9/2015 |
| CN | 107163949 A | 9/2017 |
| DE | 2335293 A1 | 1/1975 |
| GB | 1090403 A | 7/1971 |
| LV | 14791 B | 5/2014 |
| NZ | 240177 A | 6/1996 |
| WO | 9525430 A1 | 9/1995 |
| WO | 0067581 A1 | 11/2000 |
| WO | 0213615 A1 | 2/2002 |
| WO | 2006035104 A1 | 4/2006 |
| WO | 2006037636 A2 | 4/2006 |
| WO | 2006070061 A1 | 7/2006 |
| WO | 2012050857 A1 | 4/2012 |
| WO | 2013110591 A1 | 8/2013 |
| WO | 2014147528 A1 | 9/2014 |
| WO | 2015189542 A1 | 12/2015 |

OTHER PUBLICATIONS

Sierota et al. What Is Important in Selecting Phlebiopsis gigantea Strain for Commercial Use? Journal of Agricultural Science and Technology B 5 (2015) 55-64, doi: 10.17265/2161-6264/2015.01. 006 (Year: 2015).*
Amorphous Silica Powder, Nano research elements (Year: NA).*
Rotstop ® C. Frequently asked questions, Feb. 17, 2017. 1 page. Retrieved from Internet on Sep. 2, 2020. <https://bioforest.ca/>.
Rotstop ® C. Safety Data Sheet, revision No. v3.2, May 6, 2019, 8 pages. Retrieved from Internet on Sep. 2, 2020. <https://bioforest. ca/>.
European Patent Office, Search Report of EP19157566, dated Jan. 16, 2020, 2 pages.
Finnish Patent and Registration Office, Search Report of FI20190010, dated Jul. 17, 2020, 2 pages.

(Continued)

*Primary Examiner* — Frederick F Krass
*Assistant Examiner* — Ashlee E Wertz
(74) *Attorney, Agent, or Firm* — Thomas | Horstemeyer, LLP

(57) ABSTRACT

A spreading device, a powder-like mixture composition and a method tor spreading the composition for control or prevent forest pathogens on tree stumps are disclosed.

12 Claims, 7 Drawing Sheets

(56) References Cited

OTHER PUBLICATIONS

Finnish Patent and Registration Office, Search Report of Finnish patent application No. 20185135, dated Oct. 11, 2018, 3 pages.

International Search Report issued by the Swedish Patent Office for application 2050627-5, mailed Jan. 8, 2021.

Karsky D., Dry Borax Applicator: Operator's Manual, USDA Forest Service, TE02P18-Engineering Services, Jan. 1999, [retrieved Sep. 17, 2018], retrieved from <https://www.fs.fed.us/t-d/pubs/pdfpubs/pdf99342812/pdf99342812pt01.pdf> (cover page and p. 1) & <https://www.fs.fed.us/t-d/pubs/pdfpubs/pdf99342812/pdf99342812pt02.pdf> (pp. 2-6).

Pettersson M. Stump Treatment with the Root Rot Antagonist Phlebiopsis gigantea:—Sensitivity of P. gigantea Spores to High Pressure Stress—Reduced Waler Consumption for Stump Treatment, Master Thesis No. 211, Swedish University of Agricultural Sciences, Southern Forest Research Centre, Alnarp 2013, 40 pages, [retrieved on Sep. 17, 2018], retrieved from <https://stud.epsilon.slu.se/5977/7/pettersson_m_130823.pdf>.

* cited by examiner

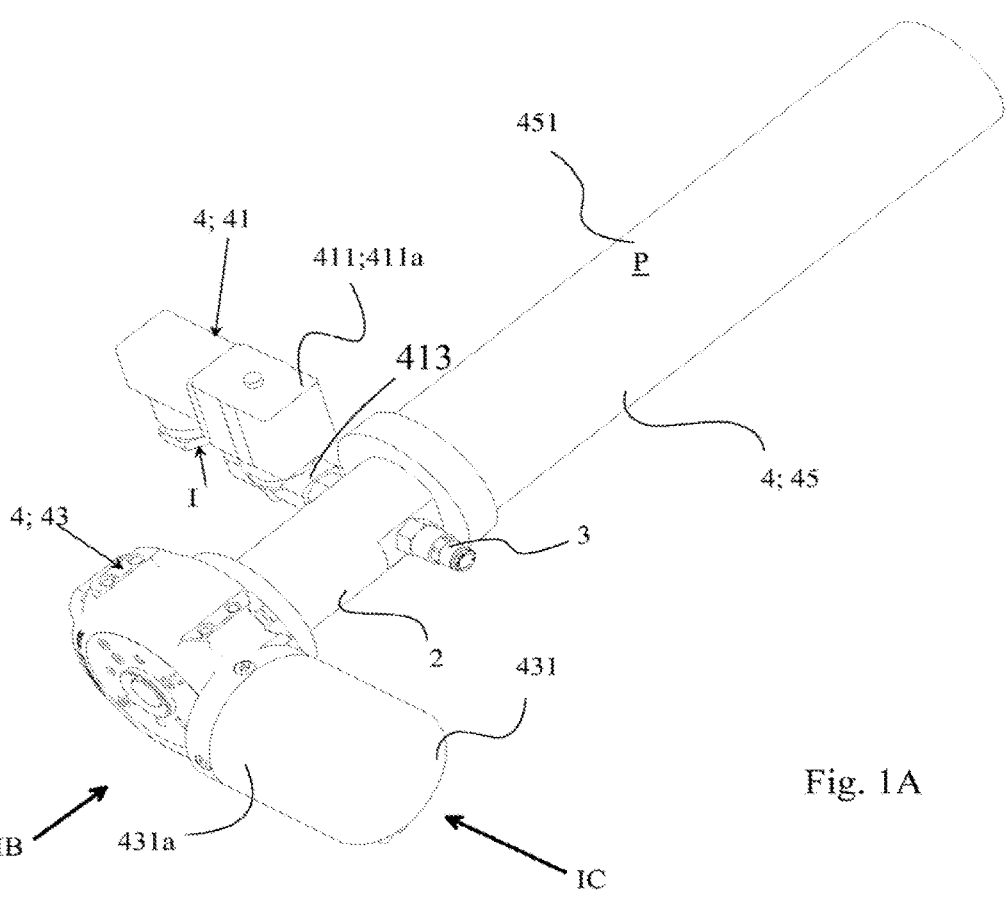
Fig. 1A
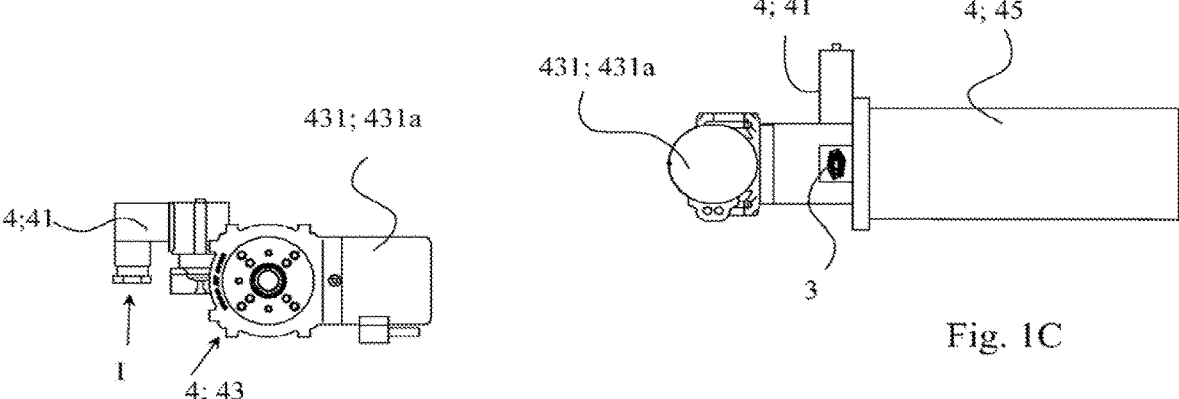
Fig. 1B
Fig. 1C

Particle size distribution of filler lime analyzed as material passing the screen

SPREADING DEVICE, METHOD AND POWDER-LIKE MIXTURE COMPOSITION FOR CONTROLLING OR PREVENTING FOREST PATHOGENS ON TREE STUMPS

CROSS-REFERENCE TO RELATED APPLICATIONS

This application is a divisional application of and claims priority to U.S. patent application Ser. No. 16/276,827, filed on Feb. 15, 2019, which claims priority to and the benefit of Finnish national patent application number 20185135, filed on Feb. 15, 2018, the entire contents of all of which are incorporated herein by reference.

FIELD OF THE INVENTION

This invention relates to methods and compositions to control or prevent growth of forest pathogens. The invention also relates to devices in use of such methods.

BACKGROUND OF THE INVENTION

Diseases of the root system are some of the most serious problems of forest and nursery trees. The major root diseases of trees are caused by wood decaying fungal pathogens that are capable of persisting long periods as saprophytes. In general, trees exhibiting good growth and vigor are resistant to root diseases while those suffering from various stresses and/or less vigor are most susceptible to root diseases. Root diseases caused, for example, by the following forest pathogens *Armillaria* species, *Heterobasidion* species, *Leptographium* species or *Phytophthora* species are widely distributed. More particularly, *Heterobasidion* species (e.g. *H. annosum*) are highly destructive and cause a root rot in most pines and butt rot inside the trunk of spruce trees. The fungus mainly spreads via airborne spores and successful infection can occur when spores germinate on a freshly cut, moist surface that is not immediately subjected to drying or heat. The fungus may then grow into the stump and roots and nearby trees through root connections. Nearly one-fourth of spruce stands in southern Finland have already been damaged by the root and butt rot fungus. The disease will spread to healthy forests unless aerial infection is prevented by treating the stumps in connection with tree felling.

Logging during the warm season, creating freshly cut stump surfaces and wounding the trees at harvest are the main reasons for rot damages in forests, which means that harvesting activity in the summertime has a strong effect on the spread of the disease. As a result of summertime logging and global warming, it is even expected that decay of spruce will further increase if infection by the root and butt rot fungus cannot be sufficiently prevented. Airborne fungal spores infect the surface of freshly cut tree stumps, where they begin to grow, and ultimately colonize the entire stump. The fungus grows into the stump and spreads along its roots to spruces nearby. This is how the disease spreads below ground to surrounding healthy trees.

Root and butt rot infection caused by *Heterobasidion* species can be prevented by performing all logging operations in the winter or by treating the exposed surfaces of the cut stumps with a protective substance in summertime logging. Since the disease cannot be completely eliminated by any procedures, it is very important to protect healthy forest stands where root and butt rot fungus is not yet established.

Prevention of root and butt rot or forest pathogens is therefore extremely important, and one important step in it is to treat the stumps created in the felling process with a substance preventing the root and butt rot fungus. There are several substances available for the treatment of tree stumps and prevention of root and butt rot, but for biological control of the pathogen, a particularly suitable product is one containing *Phlebiopsis gigantea* fungal spores in a culture medium or not, which itself is powdery but applied manually or mechanically as a solution with water. *Phlebiopsis gigantea* is a natural competitor of the root and butt rot fungus, and treating the freshly cut stumps with spores of this fungus prevents the root and but rot fungus from infecting them.

The main problem in the application of the *Phlebiopsis gigantea* fungus composition in liquid form to prevent root and butt rot by stump treatment is the large amount of water needed for application of the aqueous solution of the *Phlebiopsis gigantea* preparation on stumps in commercial logging operations. An additional problem is the limited survival of *Phlebiopsis gigantea* in an aqueous solution. Furthermore, mixing the *Phlebiopsis gigantea* preparation (i.e. spores) homogeneously with water can be problematic.

With the above prior art as a starting point, the present invention is intended to eliminate or at least alleviate the above-mentioned problems.

SUMMARY OF THE INVENTION

Thus, the object of the invention is intended to specifically provide a method and apparatus for applying microbial propagules onto a tree stump in a composition which allows considerably lower amounts of the composition containing the microbial propagules to be applied.

On a more general level, the object of the present invention is intended to provide an applicator device for administering microbial propagules onto a tree stump for controlling or preventing forest pathogens, for example bacterial or fungal pathogens. In an embodiment, the pathogens are forestry pathogenic fungi. Specifically, the object is to provide microbial propagules, which comprise spores of a *Phlebiopsis* or microbial propagules which comprise spores of *Phlebiopsis gigantea*.

Furthermore, the objective of the present invention is to provide a composition in the form of a powder-like mixture comprising *Phlebiopsis gigantea* spores in which the fungus would be more stable compared to a conventional liquid formulation comprising *Phlebiopsis gigantea* spores. In conventional liquid formulation, it has been determined that the spores survive only one or two days. However, the spores mixed with a fine-grained carrier have an enhanced stability for prolonged periods. In addition, the objective of the invention is to provide a composition in which *Phlebiopsis gigantea* spores would be homogeneously distributed. Again, on a more general level the object of the present invention is to provide a composition in the form of a powder-like mixture comprising microbial propagules in a stable form.

Accordingly, above mentioned objectives can be achieved, for example, by means of the spreading device to administer onto a tree stump a composition which comprises microbial propagule to control or prevent the growth of a forest pathogen. This spreading device comprises: a spreading end connected to a pipe-like frame, and administering means for administering said composition, wherein the administering means comprise a pressure accumulator for loading pressurized air, the pressure accumulator being connected to a first end of the spreading device's frame via a supply pipe and regulating means which comprises at least one regulating valve for regulating flow of the pressurized air entering the frame which regulating means further comprises communication means for providing to the at least one regulating valve data about starting time of pressurized air delivery and data about duration of said pressurized air delivery, wherein said pressure level delivered pressurized air depends on the diameter of the tree stump and which administering means further comprises: a powder storage which contains a powder-like mixture comprising microbial propagule and a solid fine carrier, which powder storage is configured to be capable of being brought into a flow connection of the powder-like mixture with the frame, and a control device connected to a second end of the frame for administering the powder-like mixture inside the frame and means for blowing the powder-like mixture onto a tree stump via a spreading head connected to the frame.

Further the above mentioned objectives can be achieved by means of a powder cartridge containing a powder-like mixture, which powder cartridge is adapted to be used in a spreading device disclosed herein, wherein the powder-like mixture of the powder cartridge can be brought into the flow connection with the frame of the spreading device by the usage of a control apparatus, and which powder-like mixture comprises microbial propagules and a solid fine carrier, wherein said solid fine carrier has volumetric weight of at least 0.50 g/cm$^3$, at least 0.60 g/cm$^3$ or at least 1 g/cm$^3$ and wherein amount of the powder-like mixture to be administered on a tree stump is arranged to be depend on diameter of the tree stump to be treated.

The invention also relates to a composition in the form of powder-like mixture, the composition comprising microbial propagules and a solid fine carrier and the microbial propagules being fungal spores which control or prevent the growth of forest pathogens on a tree stump and wherein said solid fine carrier has a volumetric weight of at least 0.50 g/cm$^3$, at least 0.60 g/cm$^3$, or at least 1 g/cm$^3$.

A further solution to above mentioned problems which fulfil the above objections of this invention is to provide a method to control or prevent growth of *Heterobasidion* fungal pathogen on a tree stump, the method comprising the steps of: a) providing a composition as described herein, and b) spreading or dispersing the composition in a powder-like mixture on said tree stump by a machine or manually.

Yet another solution to above mention objections of the invention is to provide a method or spreading or dispersing onto a tree stump a powder-like mixture comprising microbial propagules controlling or preventing growth of a forest pathogen, and a solid fine carrier having a volumetric weight of at least 0.50 g/cm$^3$, at least 0.60 g/cm$^3$ or at least 1 g/cm$^3$, wherein the method comprises the steps of: a) receiving data about dosage of a powder-like mixture by regulating means of a dispersing device, b) dosing the powder-like mixture to an amount which depends on the diameter of the tree stump to be treated, c) forming an aerosol from pressurized gas and the powder-like mixture by delivering pressurized gas on an adjusted amount and possible also on an adjusted rate into the powder like-mixture, d) spreading or dispersing the aerosol onto a tree stump by means of pressurized gas flow.

Specifically, the present invention relates to the use of the composition comprising the powder-like mixture for controlling or preventing growth of forest pathogens on a tree stump, which use includes the spreading or dispersing of the powder-like mixture on said tree stump by machine or manually.

The powder-like mixture comprises (or consists of) fungal spores, in the presence or not of a culture medium (S), and, additionally, a solid fine-grained carrier (K) and can include a marker dye or a nutritional supplement, or a mixture thereof. The powdery mixture of the present invention is capable of absorbing water.

As used herein, the term "microbial propagules" is intended to refer to a material that can used for the purpose of propagating an organism to the next stage in their life cycle via dispersal and comprises spores or vegetative cells of microbiological origin including all bacteria, fungi, viruses, protozoans, yeasts, slime molds, chlamydospores, hyphae, and cysts. Generally, spores in this application mean either spores of fungi or bacteria, preferably spores of fungi. As it is known in the art, "spores" are reproductive structures, usually adapted for dispersal and surviving for extended periods of time in unfavorable conditions. Fungal propagules also include conidia (also termed conidiospores or mitospores) which are asexual non-mobile spores.

In the present application, the microorganism is cultivated on a culture medium as, for example, a solid growth medium. For example, amorphous silica (i.e. silica gel) or rice can be used as a culture medium (or solid growth medium) for the cultivation of fungal spores. It can be understood that any of the well-known solid growth medium can be used in the context of the present invention. After cultivation, the colonized culture or growth medium is dried to obtain a powdery product comprising fungal spores. A colonized growth medium usually does not contain enough nutrients to promote the growth of the fungus on a tree stump. Therefore, nutritional supplements can be dispensed into the powdery-like mixture comprising fungal spores to accelerate the growth of the fungus (as, for example, the growth of *Phlebiopsis* sp.) on a tree stump as well as to improve its efficacy against the forest pathogen. Such nutritional supplements can be e.g. lignin and its derivatives such as lignosulphonates or lignohumates.

To be more precise, the invention relates to a spreading device for administering onto a tree stump a composition which comprises microbial propagules to treat or prevent pathogen, which spreading device has a spreading end connected to a pipe-like frame, and administering means for administering said composition. Administering means comprise a feeding device for pressurized air connected to the first end of the spreading device's frame and regulating means for regulating the pressure of pressurized air entering the frame, a powder storage in contact with the frame, which storage contains a powder-like mixture made up of microbial propagules and a solid fine-grained carrier, and a regulating device connected to the second end of the frame for administering the powder-like mixture (S, K) inside the frame and means for blowing the powder-like mixture (S, K) onto a tree stump, via the spreading end connected to the frame.

Preferably, the feeder apparatus comprises a powder storage with a container having powder-like mixture and means for bringing the powder-like mixture to the inside of the frame.

Advantageously the powder-like mixture of the present invention comprises microbial propagules which control or prevent the growth of *Heterobasidion* spp. More particularly, the powder-like mixture of the present invention controls or prevents the growth of *Heterobasidion occidentale, Heterobasidion irregulare, Heterobasidion parviporum* or *Heterobasidion annosum.*

In a preferable embodiment of the present invention the powder-like mixture (S, K) is made up of microbial propagules in the presence or not of the culture medium used for producing the microbial propagules and a solid fine carrier and can include a marker dye and a nutritional support. In an embodiment, the microbial propagules are free of culture medium. In an embodiment, the microbial propagules are in combination with a culture medium used for producing the microbial propagules.

Advantageously the microbial propagules are fungal spores. For example, the fungal spores are from the genera *Phlebiopsis*. In a further embodiment, the spores are from *Phlebiopsis gigantea*. An advantage of using *Phlebiopsis gigantea* is its ability to colonize a stump surface, *Phlebiopsis gigantea* grows into the stump and penetrates deep into the root system, naturally outcompeting *Heterobasidion* spp. and preventing it from becoming established or spreading.

In an embodiment, the strains of *Phlebiopsis gigantea* used in the present invention are *Phlebiopsis gigantea* strain ATCC 90304, *Phlebiopsis gigantea* strain DSMZ 26191, *Phlebiopsis gigantea* strain DSMZ 26192 or *Phlebiopsis gigantea* strain DSMZ 16201, or a combination thereof. These strains are highly effective against *Heterobasidion* spp.

In another embodiment, the powder cartridge according to present invention, which is used in a feeding device contains a powder-like mixture, which comprises microbial propagules and a solid fine carrier. In an embodiment, the volume weight (or volumetric weight or density) ratio of the solid fine carrier is at least 0.3 g/cm³ (or g/ml), 0.4 g/cm³, 0.5 g/cm³, 0.6 g/cm³, 0.7 g/cm³, 0.8 g/cm³, 0.9 g/cm³ or at least 1.0 g/cm³ or more than 1.0 g/cm³.

In a preferred embodiment of the invention, the powder cartridge available in the applicator includes powdery mixture comprising fungal spores of *Phlebiopsis gigantea* in the presence or not of a culture medium used for producing the spores and a solid fine-grained carrier having a volume weight ratio of at least 0.5 g/ml (or g/cm³). In an embodiment, the fungal spores are in the presence of the culture medium used for producing the spores. The culture medium for fungal spores comprises preferably amorphous silica.

The invention is based on the one hand to the general idea that microbial propagules, which may or may not include their culture or growth medium, are applied in the form of powder onto a tree stump in combination with a solid fine carrier having a volume weight ratio of at least 0.5 g/ml (0.5 g/cm³) in order to obtain a high density powder-like mixture. This high density powder-like mixture facilitates the application of fungal spores and their retention onto the stumps. Application of microbial propagules as a powdery mixture of the present invention makes it possible to use significantly smaller amounts of powde-rlike-mixture compared to an equivalent preparation applied as an aqueous solution while maintaining the same activity or efficacy.

On the other the present invention is based on the general idea of spreading or dispensing above mentioned microbial propagules in combination with a solid fine carrier onto a tree stump by using a spreading device which uses pressurized air for spreading microbial propagules in combination with a solid fine carrier onto tree stump. Advantageously this spreading device will receive wireless control commands relating to amount of microbial propagules in combination with a solid fine carrier and the amount and delivery time automatically from harvester head hydraulic system. Advantageously these control commands are received from hydraulic circuit which controls the hydraulic actuator connected to the use of chain saw when a standing tree is cut to a tree stump.

More particularly, fungal spores of *Phlebiopsis* (as, for example, fungal spores of *P. gigantea*) in the presence or not of amorphous silica used as a solid growth media, are applied in the form of powder onto a tree stump in combination with a solid carrier having a volume weight ratio of at least 0.5 g/ml to obtain a high density powder-like mixture. This high density powder-like mixture facilitates the application of fungal spores and their retention onto the stumps. Application of fungal spores of *Phlebiopsis* as a powder mixture makes possible to use significantly smaller amounts of powder-like mixture compared to an equivalent preparation applied as an aqueous solution while maintaining the same activity or efficacy.

It has been established that the required amount of *Phlebiopsis gigantea* spores (in combination or not with a solid growth media) is of about 25 to 100 g per hectare of harvested forest area, regardless of the application method. If the composition is in an aqueous solution, the spores of *Phlebiopsis gigantea* are mixed in water and the solution is applied at a rate of 25 to 100 liters per hectare of harvested area. Thus, the application rate of the composition comprising *Phlebiopsis gigantea* microbial propagules, in the presence or not of the culture medium used for producing the microbial propagules, in a liquid form is about 25-100 kg per hectare of harvested area.

On the other hand, the application rate of the powder-like mixture according to the present invention is only 0.25-1 kg per hectare of harvested area. This represents about ¹⁄₁₀₀ of the consumption of a similar formulation applied as an aqueous solution as described above. Both the powder-like mixture and the aqueous solution contain the same number of active spores of *Phlebiopsis gigantea*, but the spore content per unit of weight of the powder-like mixture is considerably higher than the spore content of aqueous solution per unit of weight in the aqueous solution.

The spores of *Phlebiopsis gigantea* in combination or not with the solid growth medium used for the cultivation of the fungus form a cultivation powder (or a colonized growth medium). The volume weight density of this combination is very low (e.g. if the medium is silica gel, the volume weight of the colonized growth medium is only about 0.22 g/ml), which implies that its mechanical application can be problematic as the colonized growth media sprayed on the tree stumps may easily be blown away. However, when a suitable solid carrier such as, for example lime which has a sufficiently high-volume weight (about 1.44 g/ml), is added to the colonized growth media, a powder-like mixture according to the present invention is obtained which powdery-like mixture allows a better distribution and surface colonization of the stump by the fungus.

This concept may be broadened to application of any microbial propagules as a powder mixture. Indeed, as mentioned, very light microbial propagules may easily be blown away from the tree stump by wind. Adding a suitable high volume weight (or density) solid carrier to a spore mixture will allow a better surface colonization by the microbial propagules.

From the powder-like mixture an aerosol of solid matter is formed in the spreading device by means of pressurized air, after which the powder-like mixture can be aimed at and mechanically applied to a desired location.

In addition, as mentioned, the invention achieves the significant benefit that in a powder-like mixture such as powdery mixture comprising spores of *Phlebiopsis gigantea*, fungal spores remain alive much longer than in an aqueous solution.

The use of a powder-like mixture such as a powdery mixture further achieves a significant additional benefit compared with a liquid formulation, as a powdery mixture does not need to be mixed with water at the place of use. Indeed, the powdery mixture can simply be mounted in the container of the applicator in the form of a powder cartridge and thereafter the powder contained in the powder cartridge can be delivered to the target by means of an applicator using pressurized air.

In a preferred embodiment of the invention, the powder cartridge includes a solid fine-grained carrier. As used herein, the solid carrier comprises one or more organic or inorganic carriers or a mixture thereof. Examples of inorganic carriers that could be used in the context of the present invention comprise, but are not limited to, lime, calcium carbonate, kaolin, bentonite, talc, gypsum, vermiculite, perlite, amorphous silica, granular clay or a mixture thereof. In a preferred embodiment, the solid carrier is lime or calcium carbonate. In an embodiment, the fine-grained carrier is calcium carbonate. Examples of organic carriers comprise, for example, fine-grained cellulose powder (e.g. microcrystalline cellulose), polysaccharides (chitin, chitosan, polyacrylamide), sugars, lignin derivatives, cereal flours, yeast extract, betaine or fine-grained composition made of cereal grains, bran, sawdust, peat or wood chips or a mixture thereof. Alternatively, any other suitable solid fine-grained carrier can be used in the context of the present invention.

The solid carriers used in the context of the present invention have a sufficient specific gravity (or density) to allow the powder-like mixture to be mechanically applied onto the tree stump.

For example, the volume weight density of lime or calcium carbonate is relatively high and in addition, their particle size is favorable from the standpoint of distribution of the powder mixture on the stumps. If the grain size of the carrier particles is too small, the powdery mixture easily flies away with the wind, and an excessive grain size of the carrier particles relative to the particle size of the culture powder colonized growth media in turn causes uneven spread of the powder and the fungal spores of *Phlebiopsis gigantea* therein onto the tree stump. The size distribution of the lime or calcium carbonate particles is the same order of magnitude as with the solid growth media (e.g. amorphous silica) (about 0.01 mm). Therefore, the fungal spores of *Phlebiopsis gigantea* spread evenly into the powdered mixture.

The powder-like mixture of the present invention is an inoculant comprising (or consisting of) 5 to 50 w-% of microbial propagules, 5 to 90 w-% of a solid carrier, 0 to 5 w-% of a marker dye (or a colouring substance) and 0 to 40 w-% of a nutritional supplement. In an embodiment, the powder-like mixture of the present invention comprises (or consists of) 10 to 30 w-% of microbial propagules and 20 to 80 w-% of a solid carrier and may further comprises 0.5 to 5 w-% of a marker dye (or a colouring substance) or 0.5 to 20 w-% of a nutritional supplement, or a mixture thereof. In a further embodiment, the powder-like mixture comprises (or consists of) 20 to 30% w-% of *Phlebiopsis gigantea* spores, 60 to 70 w-% of calcium carbonate, 0.5 to 3 w-% of marker dye and 0.5 to 10 w-% of a nutritional supplement.

In one preferred embodiment of the invention, the powder cartridge further comprises (or contains) microbial propagules in the presence or not of the culture medium used for producing the microbial propagules and can include a marker dye and/or supplemental nutrients. Any known supplemental nutrients can be used in the context of the present invention. For example, the supplemental nutrient is selected from a group including lignin and its derivatives such as lignosulfonate and lignohumate.

Supplemental nutrients are beneficial for starting the growth of *Phlebiopsis gigantea* spores while the dye is for marking a treated tree stump.

In the following, the invention and the benefits that can be achieved with it will be further illustrated with reference to the accompanying drawings and example 1 which describes the properties of the powder-like mixture.

SHORT DESCRIPTION OF THE FIGURES

FIG. 1A shows an applicator according to the invention in a perspective view.

FIG. 1B shows an applicator according to FIG. 1, viewed from the direction IB of FIG. 1A.

FIG. 1C shows an applicator according to FIG. 1, viewed from the direction IC of FIG. 1A.

DETAILED DESCRIPTION OF THE INVENTION

Figure 2:
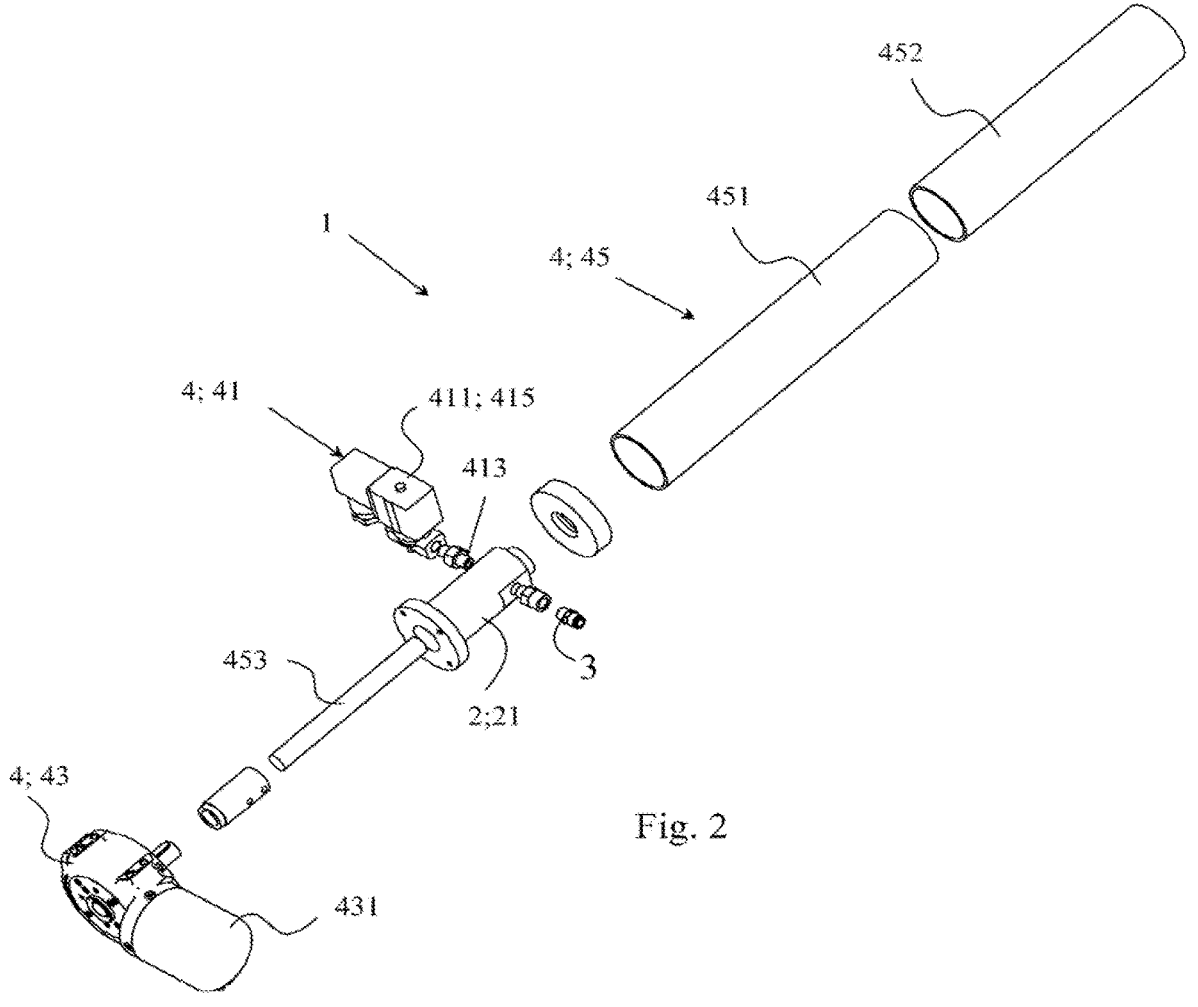
FIG. 2 shows the applicator presented in FIGS. 1A-1C as an exploded view.

In the following, the main structures of an applicator according to the invention are first described with reference to FIGS. 1-3.

FIGS. 1A-1C show fungal spore applicator (spreading device) 1 according to the invention from slightly different angles of view but without any regulating means 41 or pressure accumulator needed for controlling and storing of the pressurized air (I). The feeding of pressurized air I is illustrated in FIG. 3. FIG. 2 shows the spreading device as an exploded view.

Spreading device 1, such as aerosol applicator, has a tubular frame 2. Aerosol spreading head 3, is associated with the first end of tubular frame 2 seen in the forefront. Frame 2 also includes administering means 4 for forming a spore-containing aerosol A which is applied using spreading head 3, equipped with a back-pressure valve, onto a tree stump T. Tubular frame 2 may also include measurement means 21 such as measuring devices for measuring flow, pressure and temperature of pressurized air. Through the measurement data obtained from these measuring devices, the formation of aerosol A from the pressurized air I and the powder-like mixture S, K to be combined with it can be adjusted first. Subsequently, information received from the measuring means 21 can still be used while applying the formed aerosol A onto a tree stump in a manner described later.

Administering means 4 for dispensing of pressurized air I and powder-like mixture S, K comprises regulating means 4; 41 associated with the frame 2 of the aerosol applicator 1; for adjusting the volume flow of pressurized air I entering frame 2 via a pressurized air supply pipe 413

The volume flow of pressurized air I may be adjusted using valve 4; 415 such as solenoid valve shown in FIGS. 1A and 1B. However, in a preferred embodiment of the present invention, the volume flow of the pressurized air I is controlled automatically using a pressure accumulator 42 and electromagnetic on/off valves 411; 411a and 411; 411b shown in FIG. 3. Administering means 4 also includes pressure accumulator 42 of pressurized air I for generating and supplying pressurized air I to electromagnetic valve 411; 411a, 411b as well as further inside of the frame 2, through a short supply pipe 413 of pressurized air (compare to FIG. 3).

Administering means 4 further comprises communication means 47 (FIG. 3) for providing to the regulating means 41, preferable electromagnetic regulating valves, for example, data about starting time of pressurized air I delivery and data about pressure level of said pressurized air I. Said communication means 47 also provide the control apparatus 43 with the data relating to starting time and duration of the dosage of powder-like mixture S, K inside the frame 2. The pressure of delivered pressurized air and dosage of powder-like mixture S, K depends primarily on the diameter of the tree stump T to be sawed from a trunk (see FIG. 7). Communication means 47 are preferably wireless communication means which comprise a transmitter and a receiver of an electromagnetic signal. Suitable wireless communication means comprise a receiver in connection of electromagnetic valve or control apparatus and an electromagnetic signal transmitter in connection with chain saw hydraulic circuit 91 or in connection with a hydraulic circuit controlling the actuator affecting to a stump treatment device for liquid 97 (see FIG. 5).

Administering means 4 further comprises control apparatus 43, incorporating a stepper motor 431; 431a to dispense/dosage powder-like mixture S, K onto the inside of frame 2. The aerosol A can thereafter be formed on the inside of frame 2 and dispensed to the target, i.e. to the tree stump, by supplying a burst of pressurized air I flow inside of frame via supply pipe 413.

Figure 3:
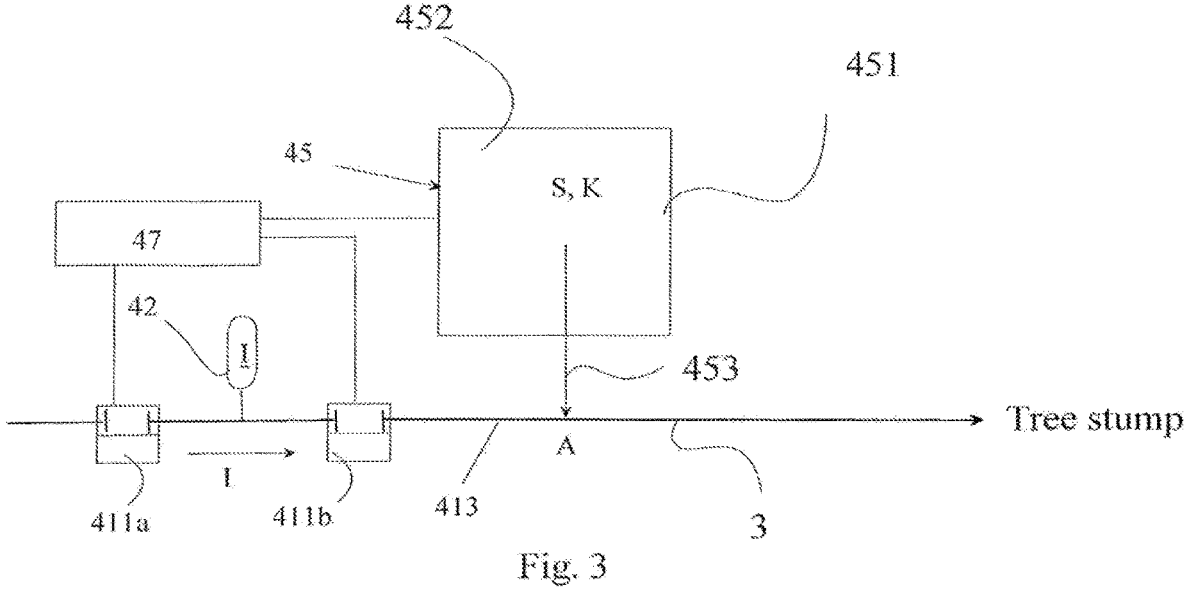
FIG. 3 shows schematically the principle of forming aerosol from dry matter.

Tubular frame 2 also includes a powder storage 4; 45 communicating with the inside of body 2 by means of supply tube 453 shown in exploded view of FIG. 2. Powder storage 45 comprises container 451 having powder cartridge 452, which contains powdery mixture being powder-like mixture S, K. The powder-like mixture S, K is composed of a mixture of *Phlebiopsis gigantea* spores, in the presence or not of the culture medium S used for producing the spores, mixed with a heavier solid powdery carrier K (compare FIG. 3). Powder storage 45 is operatively coupled with the previously described control apparatus 43 having a stepper motor 431 for dispensing and bringing the powder-like mixture S, K to the inside of frame 2 with supply tube 453. The powder-like mixture S, K arrives from container 451 to the inside of tubular frame 2 along supply tube 453.

Pressurized air I is then supplied from pressure accumulator 42 via pressurized air supply pipe 413 first to the inside of frame 2 and from there to spreading head 3.

Regulating means 41 of pressurized air I may also be used for adjusting the rate of powder-like mixture S, K coming from the powder storage 45 in a case regulating means comprises solenoid valve or like. However, normally regulating means 41 began their action only after powder-like mixture S, K have been dispended inside of the frame by means of the stepper motor 431.

The regulating means 41 are controlled by communication means 47, which are used delivering proper control commands to regulating valve(s) 411 for dispensing of pressurized air (compressed air) I and to control apparatus 43 for adjusting the dosage of powder-like mixture by the use powder cartridge 452. This is now illustrated more accurately in referring to FIGS. 3, 5, 6A-6B and 7. Powder-like mixture S, K contains fine carrier K and microbial propagules S, which, in turn, contains about 5% of water and is formed by the possible culture medium and the fungal spores.

Figure 5:
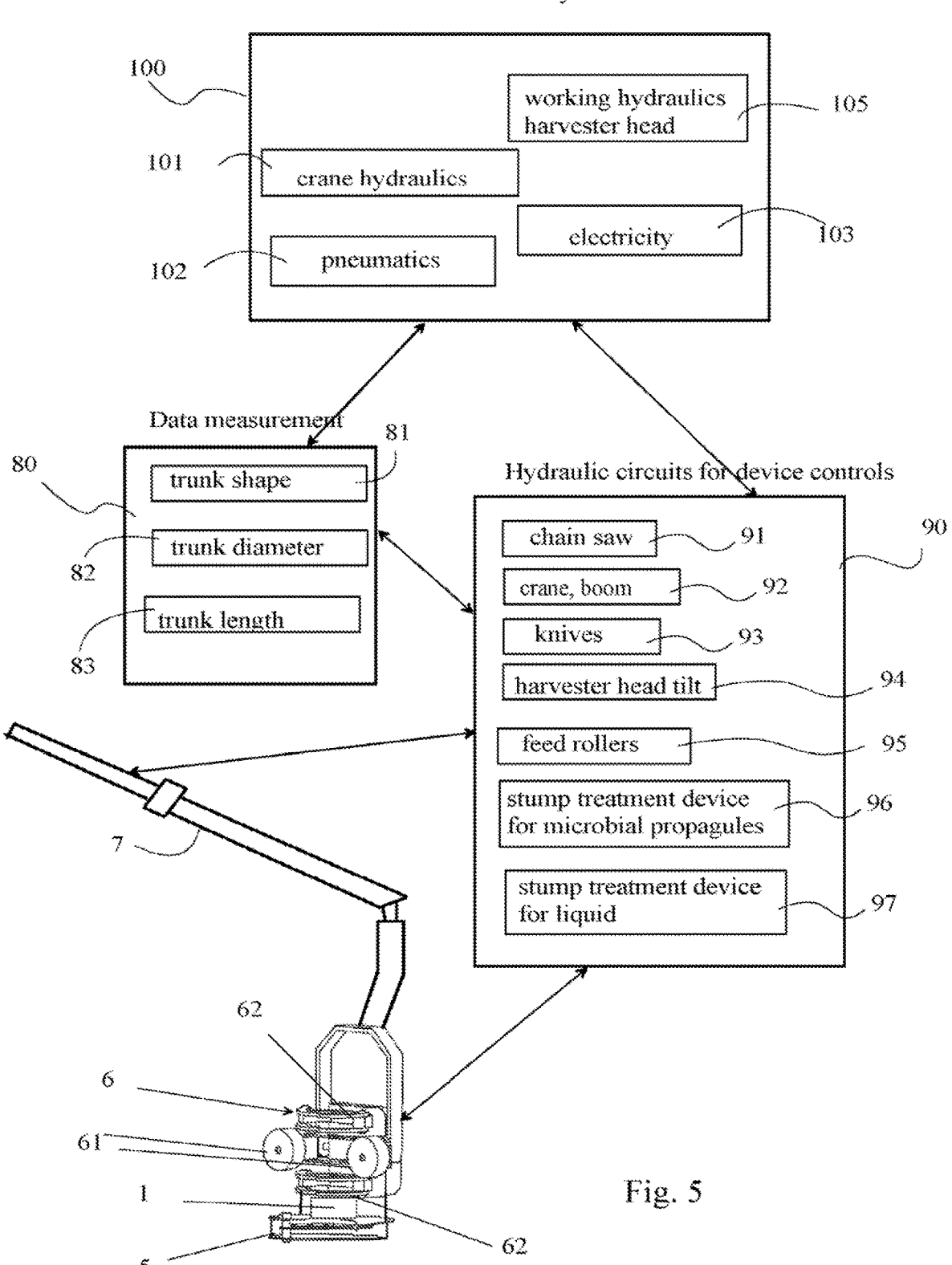
FIG. 5 illustrates schematically the control system and measurements of the harvester head.
Figure 6A:
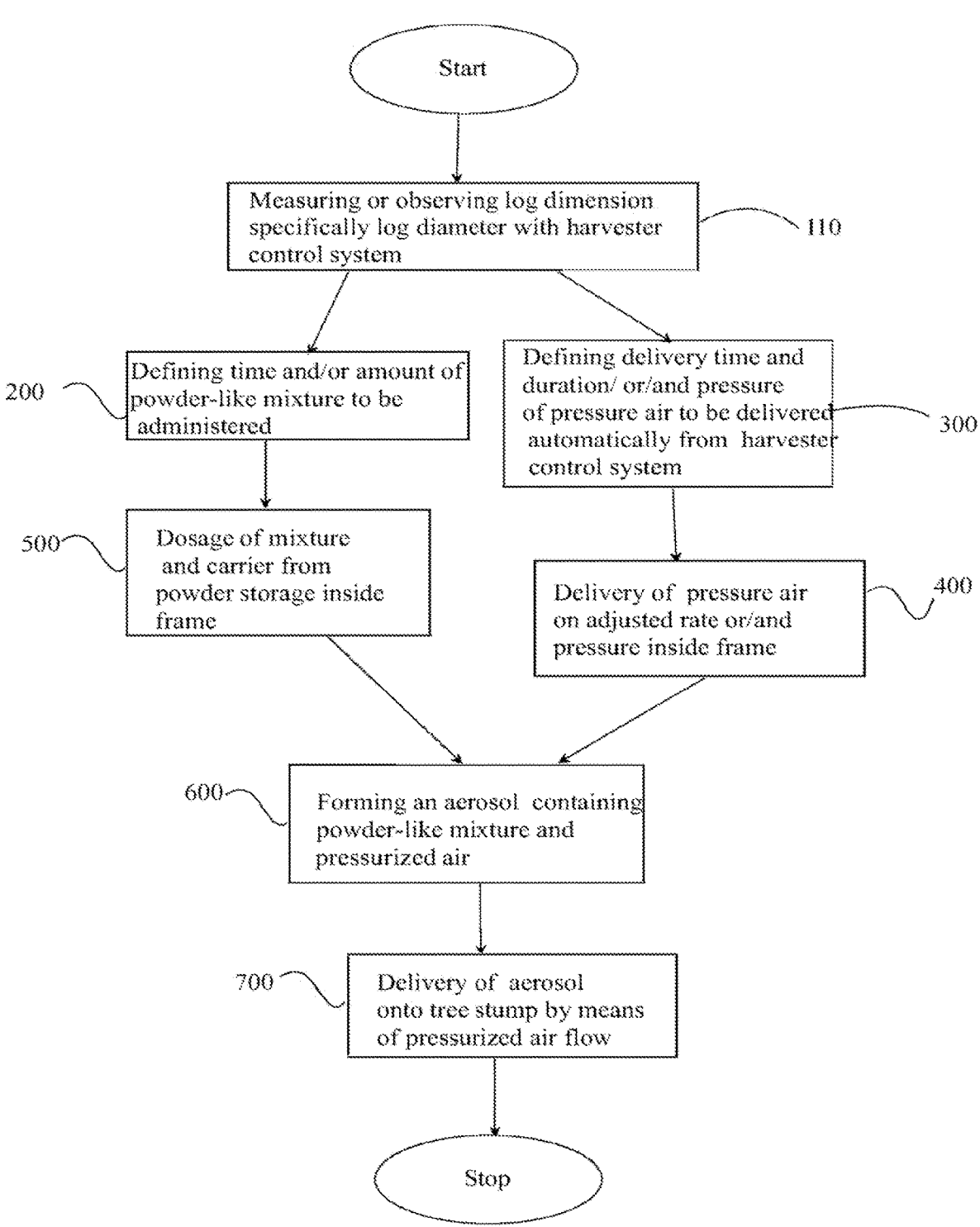
FIGS. 6A and 6B show examples of general methods of the present invention.
Figure 6B:
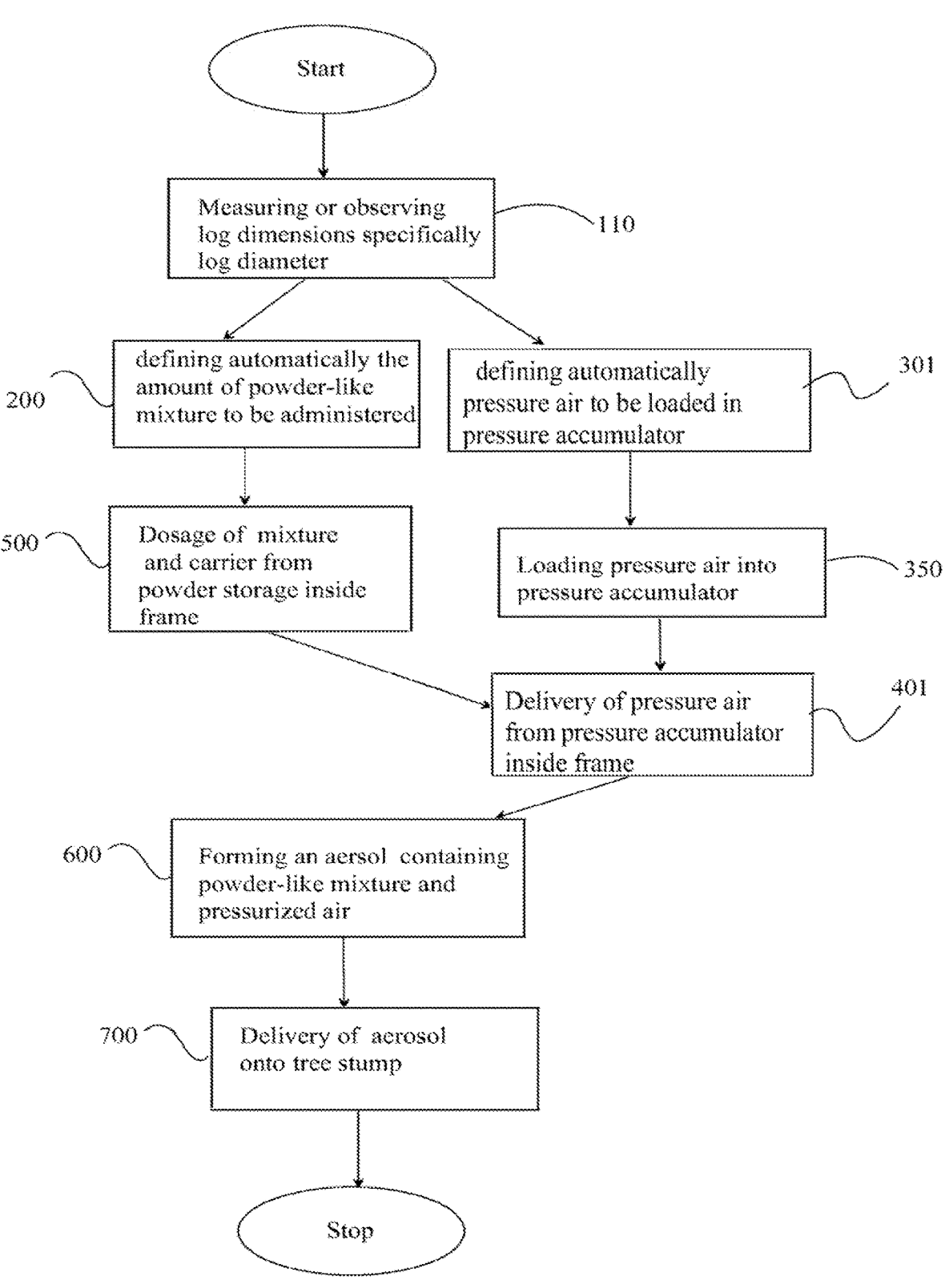

The more general method of the invention is first presented by referring to FIGS. 5, 6A-6B. Said method comprises first receiving data about dosage of the powder-like mixture (S, K) by the regulating means 41.

In a general method according to present invention in a tree stump T is spread or dispersed a powder-like mixture, which comprises microbial propagules which control or prevent the growth of a forest pathogen and a solid fine carrier having a volumetric weight of at least at least 0.50 $g/cm^3$, preferable at least 0.60 $g/cm^3$ or most preferable at least 1 $g/cm^3$. Said method comprises the following steps:

receiving data about dosage of a powder-like mixture S, K by the regulating means 41 (stage 200), dosing the powder-like mixture S, K inside the frame 2 of an amount which depends on the diameter of the tree stump (stage 500), forming an aerosol A from pressurized air I and a powder-like mixture S, K by delivering pressurized air having an adjusted level into the powder like-mixture S, K (stage 400), spreading or dispersing the formed aerosol (A) onto a tree stump by means of pressurized air (I) flow (stage 600).

As can be from the above general method, the amount of powder-like mixture S, K dispensed automatically inside the frame 2 depends on the diameter of the tree stump T (stage 300). Also, the pressure level and starting time of pressurized air I delivered automatically inside the frame 2 depends on the diameter of the tree stump T. Proper control commands to regulating means 41, which control the delivery of pressurized air I inside the frame 2 is done by the action of communication means 47. These communication means 47 operate automatically and receives data which comprise control commands for starting time of delivery, the duration of the delivery and pressure level of the pressurized air I and/or starting time and the duration of the dosage of powder-like mixture S, K from the overall harvester control system 100 presented in FIG. 5.

In FIG. 5 is schematically illustrated a part of a forest harvester. This part of forest harvester comprises crane with a boom 7 and harvester head 6. Harvester head 6 comprises harvester head tilting device (not shown), feed rollers 61, delimbing knives 62, chain saw 5, stump treatments device for liquid (urea) and stump treatment device (spreading device) 1 for microbial propagules. The latter uses pneumatics circuit whereas the other devices, which are connected to harvester head, are controlled by hydraulic circuits. Each hydraulic circuit comprises hydraulic pump driven by an electric or a combustion motor (for example diesel motor) and proper valve, piping, filter and the actuator, Actuator can be hydraulic motor, hydraulic cylinder, electric motor or like which uses harvester head 1 device. Same hydraulic pump may provide hydraulic fluid to several harvester head 6 devices.

The hydraulic circuits of different device may be controlled in different way depending on the overall harvester control system 100. For example, overall hydraulic system 100 may employ only one hydraulic pump, which then gives power to crane 92, base machine, electricity 103 and also to working hydraulics 105 of the harvester head 6 devices. There may be overall hydraulic system 100 in which many device hydraulic circuits have their own hydraulic pumps; for example each delimbing knife 62 may have their own hydraulic motor and one hydraulic pump employ each knife hydraulic motor. However, we will consider here the most common harvester control system 100 which uses the same hydraulic pump to employ all working hydraulics 105 in a harvester head 6. Working hydraulics 105 comprises then following device controls controlled by corresponding hydraulic circuits, shown in FIG. 5: Chain saw hydraulic circuit 91, knives hydraulic circuit 93, harvester head tilt hydraulic circuit 94, feed rollers hydraulic circuit 95, hydraulic circuit for stump treatment device for microbial propagules 96 and hydraulic circuit for stump treatment device for liquid 97. Each hydraulic circuit for controlling corresponding harvester head 6 device includes hydraulic pump, electromagnetic valve and proper hydraulic fluid tubes or pipe leading hydraulic fluid to actuator (hydraulic motor hydraulic cylinder) connected to this specific device.

Fluid pipes leading to harvester head device may be provided by pressure gauges for measuring fluid pressure. Control system 100 may also comprise data measurements 80, for example trunk shape measurement 81, trunk diameter measurement 82 and trunk length measurement 83. The information (data) derived from data measurement(s) can be used in combination of data derived from hydraulic circuit of a harvester head 6 device to compose control command(s) for controlling other harvester head devices. For example data derived from chain saw hydraulic circuit 91, knives hydraulic circuit 93, harvester head tilt device hydraulic circuit 94, feed rollers hydraulic circuit 95, and hydraulic circuit for stump treatment device for liquid 97 can be combined to data measurements 80 and this combined information can then be used for structuring a control command.

In the present invention it is used mainly those control commands which are derived from harvester control system 100 and which comprise control commands which relate to working hydraulics of the harvester head 6 and which specifically are derived from the hydraulics circuit 91 of the chain saw 5 or/and derived from the hydraulic circuit of the tree stump treatment device for liquid 97.

Control commands from chain saw hydraulic circuit 91 are generated by the electromagnetic valve(s) which open/close the fluid pressure connection between hydraulic pump and chain saw 5. Control commands derived from the hydraulic circuit 91 connected to the usage of chain saw 5 or/and usage of the tree stump treatment device for liquid 97 relate, for example to start/shut down chain saw motor (hydraulic motor) or to turn/swing the bar with saw chain into a saw box or out from the saw box. The saw box is connected to the harvester head 6 (see also FIG. 7).

Control commands from chain saw 5 hydraulic circuit 91 can be also generated by the pressure gauge in the pipe or tube of the hydraulic circuit 91 of the chain saw 5.

The measurement derived from the pressure gauge may indicate, for instance when the bar of the chain saw is turned back and forth when the standing tree is sawed and cut at its lowermost part. This will result a tree stump T which can be treated with liquid urea, liquid colour markings or as in the present invention, with powder-like mixture.

Those control commands derived from chain saw 5 hydraulic circuit 91 and which relate to hydraulic actuators of employing chain saw (hydraulic motor or hydraulic cylinder) are then delivered by means of communication means 47 to control apparatus 43 for the dosage of the powder-like mixture (S, K) with the stepper motor 431. Same kind of control commands are also delivered by the action of communication means 47 to regulating means for controlling first and second electromagnetic valve 411a, 411b and pressure accumulator 42.

As mentioned before communication means 47 comprise preferable from wireless transmitter-receiver systems. This kind of wireless communication means 47 based on wireless technology is widely known and we refer here to existing literature on this field. Exemplary wireless communication means 47 are transmitter using electromagnetic signals transmitted from an antenna and a proper receiver of these signals (receptor), As shown in FIG. 3 pressurized air is arranged to flow automatically inside the frame 2 and onward to the spreading end 3 from pressure accumulator 42 by means of two on/off electromagnetic valves 411.

Figure 7:
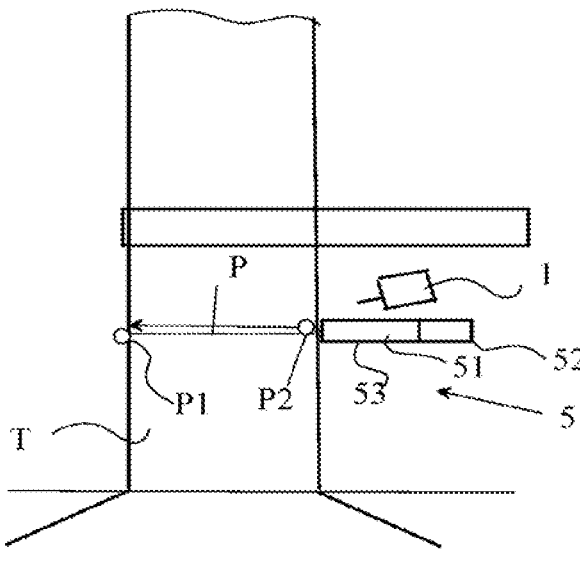
FIG. 7 illustrates schematically spreading device and a chain saw, as viewed from a side and at a beginning of the present method.

Referring now also to FIG. 7, there has been schematically presented in a side view a chain saw 5, which is connected to a harvester head 6 of the forest machine from its saw box (not shown in figure). The harvester head 1 has been placed against the standing tree and chain saw 5 has been activated the. During the tree cutting operation the bar 51 with the saw chain 53 swings out from the saw box and cuts the tree forming a tree stump T. The tree is cut so that the bar 5 moves in path P having starting point P2 and end point P1. At the end point of this path P tree has been cut and began to fell down and the bar with the saw chain swings back to the saw box. The control commands from chain saw 5 hydraulic circuit 91 is generated from hydraulic actuators which controls the actions of chain saw 5 after the chain saw 5 have reached the starting P2 at its path P in cutting a standing tree. These actuators are for example hydraulic motor for using the saw chain 53 and a hydraulic cylinder for swinging the bar. In the beginning of cutting tree, chain saw bar 51 is turned outside of the saw box connected to the harvester head 6.

Control command defining the beginning of the loading of the pressure accumulator 42 (stage 300) by opening the first electromagnetic valve 411a and also the starting point of the dosage (stage 500) of the powder-like mixture S, K containing microbial propagules and their possible culture medium S with the proper carrier K inside the frame 2 is generated by means of the control commands derived from chain saw 5 hydraulic circuit 91. This hydraulic circuit 91 controls the actuators which will be connected to actions of chain saw 5 when cutting the standing tree and forming a tree stump T.

In FIG. 7 it has been presented how bar 51 of the chain saw 5 reaches the end point P1 at its path P in sawing/cutting a tree. This event generates a new control command identifying the end of the loading of pressure accumulator 42 (stage 300) by closing the first electromagnetic valve 411a and end of dosage of powder-like mixture S, K inside frame by means of the control apparatus 43 (stage 500). The timing of the opening and closing each valve 411a, 411b depends on the diameter of the tree stump, which can be also measured in the beginning of the method, at the stage 110. However, as stated above the diameter of the tree stump T to be achieved, can also be derived from the actions of chain saw 5 when it goes in its path P from point P2 to point P1.

Control command defining the delivery time of the pressurized air I inside the frame 2 by opening the second electromagnetic valve 411b is generated by the control command which is identified or derived from the chain saw hydraulic circuit 91 when the tree began to fell and tree stump T will be formed (stage 300). Because delivering/spreading of mixture of microbial propagules and their possible culture medium S in connection with the carrier K onto the tree stump T should be made immediately after the tree stump T has been formed or when the cut tree T is still felling down this event should be connected with turning of bar 51 of the chain saw 5 back in to saw box. This event can also be connected to a certain time delay from the release of control command(s) identifying the end of the loading of accumulator 42 by closing the first electromagnetic valve 411*a*. This means that the second electromagnetic valve 411*b* is opened only after some time delay has been elapsed from the dosage of powder-like mixture S, K inside the frame 2.

The above described advantageous embodiment of the present invention is also presented in FIG. 6B: Diameter of the tree stump T is measured or will be get from the actions of chain saw when sawing a tree, in the beginning of the method at the stage 110. Powder cartridge 452 containing a powder-like mixture S, K is brought into the storage 451 of a powder feeding device 45, which powder-like mixture comprises microbial propagules and a solid fine carrier, having a volumetric weight of at least 0.50 g/cm$^3$, at least 0.6 g/cm$^3$ or at least 1.0 g/cm$^3$.

Aerosol A can then be formed from pressurized air I and powder-like mixture S, K. First is released/dosed the powder-like mixture S, K into the pressurized air I inside the frame 2 (stage 200). This is done by receiving and defining automatically data about administering time and duration of the powder-like mixture S, K from the hydraulic circuit control commands derived from chain saw 5 hydraulic circuit 91 and by transmitting these control commands to control means 43 (stage 200) which will dosage said powder-like mixture into frame by means of stepper motor 431. Due to small amount of powder-like mixture the steppermotor should be provided with a suitable reduction gear.

Powder-like mixture S, K is first brought with powder cartridge 452 having a removable cap into the container 451 of the powder storage 45. Cap is removed from the cartridge 452 which may be tube made of plastic, cardboard or thin metal. Hollow frame 2 of the spreading device 1 can be connected into flow connection of the powder-like mixture S, K via a supply tube 453. From the container 451 the powder-like mixture S, K can be dispensed by means of stepper motor 431 along the supply tube 453 to the inside of frame 2.

The amount of powder-like mixture S, K depends preferably on the diameter of the tree stump, which is measured in the beginning of the method, at the stage 110.

After the powder-like mixture S, K have been dispensed inside the frame, the pressurized air I is brought inside the frame 2—along pressurized air I supply pipe 413. Aerosol A is formed (stage 600), as shown in FIG. 3, inside of frame 2 from the powder-like mixture S, K and the pressurized air I. This pressurized air I is first loaded into pressure accumulator 42 (stage 350) by opening the first electromagnetic valve 411*a* and then delivered inside the frame by closing the first electromagnetic valve 411 and opening the second electromagnetic valve 411*b* (stage 401). Control commands defining these valve actions and loading of pressure accumulator into a certain pressure level has been described above. Shortly said, these control commands are generated from chain saw 5 hydraulic circuit 91 and transmitted to valves 411*a*, 411*b* by means of communication means 47 (stage 301).

The flow or pressurized air to the inside of the frame 2 and further into spreading head 3 is controlled by first electromagnetic valve 411*a* which is located just after pressure accumulator 42 in the flow direction of pressurized air I.

Aerosol A of dry matter formed on the inside of frame 2 is dispensed through application head 3 to the target, i.e. onto a tree stump T.

Spreading or dispersing the aerosol (A) (stage 700) to a tree stump is done by means of a pressurized air I released from the pressure accumulator 42.

Once aerosol A has been dispensed onto a tree stump through nozzles 31 of spreading head 3, the spores of *Phlebiopsis gigantea* contained in the powder-like mixture S, K begin to germinate, the fungal mycelium starts to occupy the tree stump T and prevent the growth of the root and butt rot on the tree stump.

Powder-like mixture S, K in powder cartridge 452 contains fungus spores as well culture medium S of these fungal spores as well as solid fine-grained carrier K. When the fungal spores are *Phlebiopsis gigantea* spores, their culture medium may be, for example, powdery silica gel. The fungal spores associated with the culture medium have a particle size of about 10 μm and therefore the particle size K of the fine-grained carrier K should be of the same order of magnitude as the relatively dry powder S.

Figure 4:
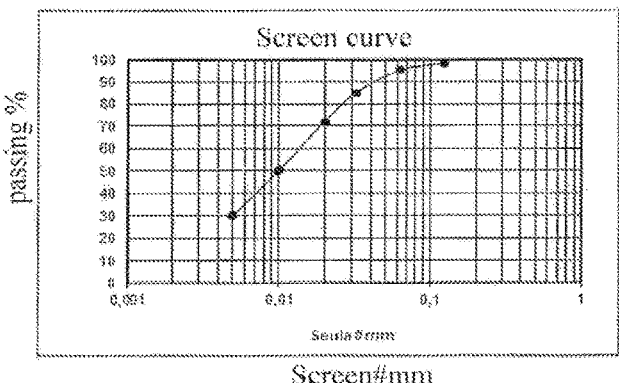
FIG. 4 shows a sieve analysis of lime.

FIG. 4 further presents a screen chart showing the particle size distribution of a preferred fine-grained carrier K, i.e. lime filler. FIG. 4 presents on the vertical axis (Y axis) the pass-through percentage of powder passing the screen, and the size of openings of the screen respectively on the horizontal axis (x-axis). As seen from FIG. 4, the particle size of lime according to a screen analysis is approximately equal to the particle size of the culture medium and the fungal spores of *Phlebiopsis gigantea*, whereby a homogeneous, dry powdery mixture S, K can be formed of lime, culture medium (silica gel) and fungal spores *Phlebiopsis gigantea*.

Table 1 further shows volume weights of some powdery substances. Of these powdery substances, Rotstop contains silica gel and fungal spores, and ammonium lignosulphonate can be used as an additive in a powdery mixture. Other powder-like substances (such as, for example but not limited to, lime, gypsum, kaolin) shown in Table 1, could be used as a solid carrier K in a powder-like mixture according to the invention to transfer the dry powder formed by fungal spores and the culture medium onto the target, i.e. a tree stump. As shown in Table 1, the volume weight of lime is about 1.44 g/ml, so it is sufficiently heavy to carry the mixture of fungal spores and their culture medium to the target, i.e. the tree trunk. Gypsum and kaolin may also be used as a solid carrier K, although their volume weight is somewhat lower than that of lime (volume weight of phosphogypsum is 1.04 g/ml and of kaolin, 0.58 g/ml, compare Table 1). The volume weight of the solid carrier K should at least be approximately 0.50 g/ml, however preferably at least 1 g/ml. As can be seen, the Rotstop powder, which mainly contains fungal spores and the medium (silica gel) used to grow them, has a relatively low volume weight of only about 0.22 g/ml, whereby the spreading of a dry matter aerosol A onto a tree stump matter containing it alone could be troublesome, at least in windy conditions. It has further been demonstrated that *Phlebiopsis gigantea* colonizes well the stump surface, even without a liquid carrier, as there is enough moisture on the freshly cut stump surface to allow for this. However, to ensure a proper density of fungal spores across the stump surface, the total volume of powder applied has to be increased by adding a carrier.

TABLE 1

| Densities of some ingredients contained in the powder-like mixture S, K. | | |
|---|---|---|
| Material/density | g/ml | g/l |
| Ammonium lignosulphonate | 0.60 | 604 |
| Filler lime (Nordkalk) | 1.44 | 1442 |
| Phosphogypsum (Siilinjärvi) | 1.04 | 1043 |
| Kaolin (standard porcelain) | 0.58 | 583 |
| Rotsop WP | 0.22 | 220 |

Only some embodiments of the invention have been described above and it will be apparent to those skilled in the art that the invention can be implemented in many other ways within the scope of the inventive idea set forth in the claims.

Dispensing of aerosol A can be done for example by using a servo motor or like with a feedback instead of a stepping motor. Control valve 411 may in some cases also be a damper plate.

Besides fungal spores and their culture medium as well as fine-grained carrier substance K, the powdery mixture S, K contained in powder cartridge 452 may also preferably contain dye and supplemental nutrients. The supplemental nutrients are preferably selected from a group including lignin and its derivatives such as lignosulphonate and lignohumate and those will help increase the growth rate of fungal spores on a tree stump. In powdery mixture S, K the activity of the fungal spores remains at a high level significantly longer than in a solution-based product.

The powder-like mixture S, K blown onto the tree stump with aerosol A should be water-absorbent so that the fungal spores will adhere properly. Water absorption can be increased either by selecting a suitable water absorbing culture medium for fungal spores (for example silica gel) or a suitable fine-grained carrier.

EXAMPLE

Study Comparing the Efficacy of Liquid and Solid Formulation of *Phlebiopsis Gigantea* Spores The upper surfaces of freshly cut billets of Norway spruce were treated with powder containing *Phlebiopsis gigantea* (strain ATCC 90304) spores. Spores were obtained by cultivating *Phlebiopsis gigantea* on solid silica carrier and drying the colonized growth medium. Inert carriers, calcium carbonate and ammonium lignosulphonate, were mixed with the dry growth medium to obtain the following powder formulation:

25% *P. gigantea* spores on silica

65% $CaCO_3$

10% ammonium lignosulphonate

The surface of each billet (length about 30 cm, diameter 14-18 cm) was divided in two sectors, one section was treated with the powder mixture comprising the fungal spores and a root rot fungus *Heterobasidion parviporum*, and the second section was treated only with *Heterobasidion parviporum*.

Two powder application rates were studied, 1.0 and 2.0 $mg/cm^2$. Control billets were treated with a commercial stump treatment agent, Rotstop SC, as a 1 g/l water suspension. The billets were kept in open air for 2.5 months. Then the billets were cut 5 cm below the surface and a 2 cm thick disc was taken, incubated in a plastic bag for one week and analyzed under a dissecting microscope for *Heterobasidion* covered area based on conidiophore development during the incubation. Only discs where an established *Heterobasidion* infection in the control side was observed were taken into account in calculation of the results.

TABLE 2

| | | | Area treated with the product and *Hererobasidion* | | | Control area treated with *Hererobasidion* only | | | Efficacy |
|---|---|---|---|---|---|---|---|---|---|
| Number of discs | Discs with no *Heterobasidion* | | Total disc | Infested area | | Total disc | Infested area | | of |
| pcs | pcs | % | area $cm^2$ | $cm^2$ | % | area $cm^2$ | $cm^2$ | % | treatment |
| Powder, 1 mg/cm2 | 21 | 16 | 76% | 1428 | 1.62 | 0.113% | 1488 | 20.53 | 1.38% | 92% |
| Powder, 2 mg/cm2 | 24 | 22 | 92% | 1596 | 1.75 | 0.110% | 1799 | 27.53 | 1.53% | 94% |
| Rotstop suspension | 23 | 14 | 61% | 1394 | 1.34 | 0.096% | 1520 | 48.59 | 3.20% | 97% |

Area infested with *Heterobasidion* in spruce discs treated with different preparations containing *Phlebiopsis gigantea* in comparison with control discs with *Heterobasidion* only.

The results show that all the preparations containing *Phlebiopsis gigantea* controlled *Heterobasidion* root rot fungus very effectively. The efficacy was over 90% with all the treatments. Efficacy of the treatment with the powder formulation was comparable to the treatment with the commercial stump treatment method which is in an aqueous formulation.

REFERENCE NUMBER LIST

1 Spreading device
2 Frame
21 measurement means
3 spreading head
31 nozzles
4 Administering means
41 regulating means
411 regulating valve(s)
411*a* first electromagnetic valve
411*b* second electromagnetic valve
413 (pressurized) air supply pipe
42 pressure accumulator
43 control apparatus
431 stepper motor
45 powder storage
451 container

452 powder cartridge
453 supply tube
47 communication means
5 Chain saw
51 bar
52 bar holder
53 chain
6 Harvester head
7 Boom
80 Data measurement
81 trunk shape
82 trunk diameter
83 trunk diameter
90 Hydraulic circuit
91 chain saw
92 crane, boom
93 knives
94 harvester head tilt
95 feed rollers
96 stump treatment device for microbial propagules
97 stump treatment device for liquid
100 Harvester control system
101 crane hydraulics
102 pneumatics
103 electricity
105 working hydraulics for harvester head
I Compressed air
K Carrier
P Path of the bar
P1 End point of the path
P2 Starting point of the path
S Mixture of microbial propagules and their culture medium
Mixture of fungal spores and their culture medium
S, K Powder-like mixture
T Tree stump
Following are particular embodiments of the disclosed invention.

E1. Spreading device (1) for administering onto a tree stump a composition which comprises microbial propagules to treat or prevent pathogen, which spreading device has a spreading end (3) connected to a pipe-like frame (2), and administering means (4) for administering said composition, characterized in that the administering means (4) comprise a feeding device (42) for pressurized air connected to the first end of the spreading device's (1) frame (2) and regulating means (41) for regulating the volumetric flow of pressurized air (I) entering the frame, a powder storage (45) in contact with the frame (2), which storage contains a powder-like mixture (S, K) made up of microbial propagules and a solid fine carrier (K), and a regulating device (43) connected to the second end of the frame (2) for administering the powder-like mixture (S, K) inside the frame (2) and means for blowing the powder-like mixture (S, K) onto a tree stump, via the spreading end (3) connected to the frame (2).

E2. The spreading device (1) according to E1, characterized in that powder-like mixture (S, K) comprises microbial propagules which prevents the growth of *Heterobasidion*.

E3. The spreading device (1) according to E1 or E2, characterized in that powder-like mixture (S, K) is made up of microbial propagules, its possible culture medium (S) and a solid fine carrier (K).

E4. The spreading device (1) according to E1-E3, characterized in that microbial propagules is made up of fungal spores.

E5. The spreading device (1) according to E1, characterized in that the powder storage (45) comprises a container (451), which contains a powder-like mixture (S, K), and means (453) for bringing said powder-like mixture (S, K) inside the frame (2).

E6. The spreading device (1) according to E1, characterized in that the regulating means (41) of the administering means (4) comprise a regulating valve (411) for altering the volumetric flow of pressurized air (I) entering the frame (2).

E7. The spreading device (1) according to E6, characterized in that the regulating valve (411) comprises a magnetic valve (411*a*) and/or a damper.

E8. The spreading device (1) according to E1, characterized in that the regulating device (43) comprises a stepper motor (431) or a servo motor.

E9. The spreading device (1) according to E1, characterized in that the powder storage (45) comprises a container (451), on the inside of which a powder cartridge (452) can be installed, which cartridge (452) comprises a powder-like mixture of microbial propagules, and a fine solid carrier (K).

E10. The spreading device (1) according to claim 9, characterized in that the container (451) is connected to the inside of the frame (2) via a feeding pipe (453).

E11. The spreading device (1) according to E9, characterized in that powder cartridge (452) comprises a powder-like mixture (S, K), made up of microbial propagules, its culture medium (S) and a solid fine carrier (K).

E12. The spreading device (1) according to E9-E11, characterized in that microbial propagules is made up of fungal spores.

E13. The spreading device (1) according to E11 or E12, characterized in that the fungal spores' culture medium comprises silica gel.

E14. The spreading device (1) according to E12 or E13, characterized in that fungal spores comprises spores of *Phlebiopsis gigantea*.

E15. The spreading device (1) according to E9-E14, characterized, the volumetric weight of solid fine (K) carrier is at least 0.50 g/ml, preferably at least 0.60 g/ml most preferably at least 1 g/ml.

E16. The spreading device (1) according to E9-E15, characterized in that the powder cartridge (452) contains a solid fine carrier, which is selected from the group consisting of lime ($CaCO_3$), plaster and kaolin.

E17. The spreading device (1) according to E9-E16, characterized in that the powder cartridge (452) additionally contains a colouring substance and nutritional supplements.

E18. A powder cartridge (452) available for use in a feeding device (45) of a spreading device (1) according to E1 and E9, characterized in that the powder cartridge (452) contains a powder-like mixture, which comprises microbial propagules and a solid fine carrier, the characteristic weight of which is at least 0.5 g/ml, preferably at least 0.6 g/ml most preferably 1.0 g/ml.

E19. The powder cartridge (452) according to E18, characterized in that the solid fine carrier (S) is selected from a group consisting of lime, plaster and kaolin.

E20. The powder cartridge (452) according to E18 or 19, characterized in that the powder-like mixture additionally contains a colouring substance and nutritional supplements.

E21. The powder cartridge (452) according to E20, characterized in that the nutritional supplement comprising lignin and its derivatives, such as lignosulphonate and lignohumate.

E22. The powder cartridge (452) according to E18-E24, characterized in that the powder cartridge contains 5-30 w-% of a mixture of microbial propagules, 60-90 w-% solid carrier and 1-10 w-% colouring substance and nutritional supplements.

E23. The powder cartridge (452) according to E18-E22, characterized in that the microbial propagules are fungal spores which prevents the growth of *Heterobasidion*.

E24. The powder cartridge (452) according to E23, characterized in that the fungal spores are spores of *Phlebiopsis gigantean* and said powder cartridge contains additionally the culture medium.

E25. The powder cartridge (452) according to E24, characterized in that the fungal spores' culture medium comprises silica gel.

E26. The powder cartridge (452) according to any of the E18-E25, characterized in that the powder cartridge contains 70 w-% lime, 20 w-% of a mixture of *Phlebiopsis gigantea* fungal spores and their culture medium (S), and 10 w-% colouring substance and nutritional supplements.

E27. A composition in the form of a powder-like mixture (S, K), which comprises microbial propagules and a solid carrier, the volumetric weight of which is at least 0.50 g/ml, preferably at least 0.60 g/ml most preferably at least 1.0 g/ml.

E28. The composition according to E27, characterized in that the powder-like mixture (S, K) contains a solid carrier, which is selected from the group consisting of lime, ($CaCO_3$), plaster and kaolin.

E29. The composition according to E27 or E28, characterized in that the powder-like mixture (S, K) additionally contains a colouring substance and nutritional supplements.

E30. The composition according to E29, characterized in that the nutritional supplement comprises lignin and its derivatives, such as lignosulphonate and lignohumate.

E31. The composition according to any of the E27-E30, characterized in that the microbial propagules are fungal spores which prevents the growth of *Heterobasidion*.

E32. The composition according to E31, characterized in that the fungal spores are spores of *Phlebiopsis* gigantean which composition contains additionally the culture medium.

E33. The composition according to E32, characterized in that the fungal spores' culture medium comprises silica gel.

E34. The composition according to E27-E33, characterized in that it contains 5-30 w-% of a mixture of *Phlebiopsis gigantea* fungal spores and their culture medium (S), 60-90 w-% solid carrier (K) and 1-10 w-% colouring substance and nutritional supplements.

E35. The composition according to E27-E34, characterized in that the composition contains 70 w-% lime, 20 w-% of a mixture of *Phlebiopsis gigantea* fungal spores and their culture medium (S), and 10 w-% colouring substance and nutritional supplements.

E36. Use of any composition according to E27-E35, which comprise a powder-like mixture (S, K) for treating pathogens or preventing growth of pathogens.

E37. The use of E36 wherein pathogen is fungal pathogen.

E38. The use of E36 wherein pathogen is Heterobasidon.

E39. Use of a composition comprising a powder-like mixture (S, K) according to E27-E35 for treating pathogens or preventing growth of pathogens on a tree stump, which use includes the spreading or dispersing of the powder-like mixture on said tree stump by machine or manually.

E40. The use of E39 wherein pathogen is fungal pathogen.

E41. The use of E40 wherein pathogen is Heterobasidon.

E42. The use according to E39-E41 wherein 250-1000 g of the powder-like mixture is spread onto the tree stumps per hectare of logging area.

E43. A method for spreading or dispersing onto a tree stump a powder-like mixture comprising microbial propagules and a solid fine carrier, the volumetric weight of which is at least 0.50 g/ml, more preferably 0.6 g/ml most preferably 1.0 g/ml, wherein the method comprises the following steps:

generating an aerosol (A) containing a solid matter from pressurized gas and a powder-like mixture, which comprises microbial propagules and a solid fine carrier, the characteristic weight of which carrier is at least 0.50 g/ml, more preferably 0.6 g/m I most preferably 1.0 g/ml, spreading or dispersing the aerosol (A) containing solid matter to a tree stump by means of a pressurized gas.

E44. The method according to E43, characterized in that the pressurized gas is pressurized air (I).

E45. The method according to E43 or E44 for spreading or dispersing onto a tree stump a powder-like mixture comprising microbial propagules and a solid fine carrier, the characteristic weight of which carrier is at least 0.50 g/ml, more preferably 0.6 g/ml most preferably 1.0 g/ml, with a spreading device (1) defined in claim 1, characterized in that the method comprises the following steps:

bringing a powder cartridge (452) containing a powder-like mixture into the storage (451) of a powder feeding device (45), which powder-like mixture comprises, in addition to microbial propagules a solid fine carrier (K), the characteristic weight of which is at least 0.50 g/ml, more preferably 0.6 g/ml most preferably 1.0 g/ml, manufacturing an aerosol (A) containing solid matter from pressurized air (I) and the powder-like mixture, by releasing the powder-like mixture into the pressurized air (I) inside the frame (2), spreading or dispersing the aerosol (A) to the tree stump by means of the pressurized air (I) contained in the aerosol (A).

E46. The method according to E43-E45, characterized in that the method further comprises arranging pressurized air (I) to flow inside the frame (2) and onward to the spreading end (3) by means of the regulating means (41) for pressurized air.

E47. The method according to E43-E46, characterized in that the method comprises administering the powder-like mixture into the pressurized air (I) inside the frame (2) by means of the regulating device (43).

E48. The method according to E43-E47, characterized in that the microbial propagules are fungal spores which prevents the growth of *Heterobasidion*.

E49. The method according to E48, characterized in that the fungal spores are spores of *Phlebiopsis* gigantean and said powder cartridge contains additionally the culture medium.

E50. The method according to E49, characterized in that the fungal spores' culture medium comprises silica gel.

E51. The method of E50, characterized in that fungal spores are spores of *Phlebiopsis* gigantean with possible culture medium.

E52. A powder-like mixture spread or dispersed onto a tree stump, which comprises fungal spores and culture medium of *Phlebiopsis gigantea* (S) and additionally a solid fine carrier (K), which powder-like mixture has absorbed water so that its characteristic weight has grown compared to the characteristic weight of the powder-like mixture contained in the powder cartridge (452).

The invention claimed is:

1. A composition in the form of a powder mixture, which comprises microbial propagules and a solid carrier, wherein the volumetric weight of the solid carrier is at least 0.50 $g/cm^3$, wherein said microbial propagules are fungal spores of *Phlebiopsis gigantea* and their culture medium, characterized in that it contains 5-30 w-% of a mixture of *Phlebiopsis gigantea* fungal spores and their culture medium, 60-90 w-% solid carrier and 1-10 w-% colouring substance and nutritional supplements and wherein said composition is spread as a powder form.

2. The composition according to claim 1, further comprising 0.5 to 5 w-% of a marker dye or 0.5 to 20 w-% of a nutritional supplement, or a mixture thereof.

3. The composition of claim 1, wherein the culture medium comprises amorphous silica.

4. The composition according to claim 1, wherein said fungal spores are spores of *Phlebiopsis gigantea* strain ATCC 90304, *Phlebiopsis gigantea* strain DSMZ 26191, *Phlebiopsis gigantea* strain DSMZ 26192, *Phlebiopsis gigantea* strain DSMZ 16201, or a combination thereof.

5. The composition according to claim 1, wherein said solid carrier is lime, calcium carbonate, kaoline, bentonite, talc, gypsum, chitosan, vermiculite, perlite, amorphous silica, granular clay, fine-grained cellulose powder, polysaccharides, chitin, chitosan, polyacrylamide, lignin derivatives, cereal flours, yeast extract, betaine or fine-grained composition made of cereal grains, bran, sawdust, peat or wood chips or a mixture thereof.

6. The composition according to claim 1, wherein the volumetric weight of the solid carrier is at least 0.6 g/ml.

7. The composition according to claim 1, wherein the volumetric weight of the solid carrier is at least 1.0 g/ml.

8. A method to control or prevent or control growth of Heterobasidon fungal pathogen on a tree stump, the method comprising the steps of: a) providing a composition according to claim 1; and b) spreading or dispersing of the composition in a powder mixture on said tree stump by machine or manually, wherein the spreading in step b) is at least 1 $mg/cm^2$ of the powder mixture is spread onto the tree stumps of a logging area.

9. The method of claim 8, wherein the composition in step a) comprises 5 to 30 w-% of fungal spores and 60 to 90 w-% of a solid carrier.

10. The method of claim 8, wherein said composition comprises 10 to 30 w-% of fungal spores and 60 to 90 w-% of a solid carrier.

11. The method of claim 10, wherein said composition comprises 0.5 to 5 w-% of a marker dye or 0.5 to 20 w-% of a nutritional supplement, or a mixture thereof.

12. The method of claim 8, wherein said composition comprises 10 to 30 w-% of fungal spores, 60 to 90 w-% of a solid carrier, and 0.5 to 5 w-% of a marker dye or 0.5 to 20 w-% of a nutritional supplement comprising lignin or lignin derivatives, or a mixture thereof.

\* \* \* \* \*